United States Patent [19]

Kolts et al.

[11] Patent Number: 5,210,357

[45] Date of Patent: May 11, 1993

[54] COMPOSITION OF MATTER AND METHOD OF OXIDATIVE CONVERSION OF ORGANIC COMPOUNDS THEREWITH

[75] Inventors: John H. Kolts, Ochelata, Okla.; James B. Kimble, Bartlesville, Okla.

[73] Assignees: Phillips Petroleum Company, Bartlesville, Okla.; Atlantic Richfield Company, Los Angeles, Calif.

[21] Appl. No.: 742,337

[22] Filed: Jun. 7, 1985

[51] Int. Cl.$^5$ .............................. C07C 2/00; C07C 5/00
[52] U.S. Cl. ........................... 585/500; 585/425; 585/417; 585/418; 585/541; 585/654; 585/656; 585/657; 585/658; 585/661; 585/700; 585/943
[58] Field of Search ............... 585/415, 417, 418, 500, 585/541, 654, 656, 657, 658, 661, 700, 943

[56] References Cited

U.S. PATENT DOCUMENTS

| | | | |
|---|---|---|---|
| 1,863,212 | 6/1932 | Winkler | 585/415 |
| 3,119,881 | 1/1964 | Hodgson | 585/414 |
| 3,396,206 | 8/1968 | Scott | 585/435 |
| 3,472,890 | 10/1969 | Evans | 558/375 |
| 3,557,235 | 1/1971 | Henry et al. | 585/319 |
| 3,810,953 | 5/1974 | Cichowski | 585/658 |
| 3,845,156 | 10/1974 | Farka | 585/658 |
| 4,031,128 | 6/1977 | Khcheyan et al. | 558/375 |
| 4,205,194 | 5/1980 | Mitchell, III et al. | 585/500 |
| 4,239,658 | 12/1980 | Mitchell, III et al. | 585/943 |
| 4,254,293 | 3/1981 | Tremont et al. | 585/428 |
| 4,368,346 | 1/1983 | Eastman | 585/658 |
| 4,443,644 | 4/1984 | Jones et al. | 585/500 |
| 4,443,645 | 4/1984 | Jones et al. | 585/500 |
| 4,443,646 | 4/1984 | Jones et al. | 585/500 |
| 4,443,647 | 4/1984 | Jones et al. | 585/500 |
| 4,443,648 | 4/1984 | Jones et al. | 585/500 |
| 4,443,649 | 4/1984 | Jones et al. | 585/500 |
| 4,444,984 | 4/1984 | Jones et al. | 585/500 |
| 4,450,310 | 5/1984 | Fox et al. | 585/500 |
| 4,450,313 | 5/1984 | Eastman et al. | 585/624 |
| 4,465,893 | 8/1984 | Olah | 585/943 |
| 4,482,646 | 11/1984 | Eastman et al. | 502/324 |
| 4,497,970 | 2/1985 | Young | 585/417 |
| 4,499,324 | 2/1985 | Gaffney | 585/500 |
| 4,523,049 | 6/1985 | Jones et al. | 585/500 |
| 4,523,050 | 6/1985 | Jones et al. | 585/415 |

FOREIGN PATENT DOCUMENTS 3237079 4/1984 Fed. Rep. of Germany.

OTHER PUBLICATIONS

Hinsen et al., "Oxidative Dehydrogenation and Coupling of Methane", 8th International Congress on Catalysis, vol. III, pp. 581-592, 1984.

Keller and Bhasen, "Synthesis of Ethylene Via Oxidative Coupling of Methane", J. of Catalysis, 73, 9-19 (1982).

Hinsen and Baerns, "Oxidative Kopplung, von Methan zu $C_2$-Kohlenwasserstoffen in Gegenwart unterschiedlicher Katalysatoren", Chemical Feitung, vol. 167, No. 748, 1983.

Fang and Yeh "Catalytic Pyrolysis of Methane", J. of Chinese Chemical Society, 29, 265-273 (1981).

Primary Examiner—Patrick P. Garvin
Assistant Examiner—E. D. Irzinski

[57] ABSTRACT

A solid composition of matter selected from the group consisting of:

(a) a component comprising: (1) an oxide of lanthanum and a component comprising: (2) at least one material selected from the group consisting of halogen ions, compounds containing halogen ions, tin and compounds containing tin; and (b) a component comprising: (1) at least one material selected from the group consisting of Group IA metals and compounds containing said metals, a component comprising: (2) at least one metal selected from the group consisting of lanthanum and compounds containing lanthanum and, optionally, a component comprising: (3) at least one material selected from the group consisting of halogen ions, compounds containing halogen ions, tin and compounds containing tin, and a method for the oxidative conversion of organic compounds to other organic compounds, particularly in the presence of a free oxygen containing gas. When the method is carried out in the presence of a free oxygen containing gas, a contact material including a Group IA metal, tin and, optionally, chloride ions has, also been found to be effective.

16 Claims, No Drawings

COMPOSITION OF MATTER AND METHOD OF OXIDATIVE CONVERSION OF ORGANIC COMPOUNDS THEREWITH

The present invention relates to an improved composition of matter. In a more specific aspect, the present invention relates to an improved solid contact material for the oxidative conversion of organic compounds to other organic compounds and a method of oxidative conversion therewith. In yet another aspect, the present invention relates to the oxidative conversion of organic compounds to other organic compounds in the presence of a free oxygen containing gas.

BACKGROUND OF THE INVENTION

Numerous processes are in use and have been proposed for the conversion of organic compounds and feedstocks to more valuable organic compounds and more valuable feedstocks for use in the organic chemical and petrochemical industries, particularly organic compounds and feedstocks derived from petroleum sources.

One promising approach to such conversion has been the oxidative conversion of organic compounds to other organic compounds. However, in many cases, such oxidative conversion processes are not commercially viable, primarily because they are energy intensive, conversions of the feedstock are low, selectivity to the desired compounds is low and such processes cannot be utilized in a continuous manner. In most of such processes the feedstocks are contacted with a solid contact material. However, there is a difference of opinion among workers in the art concerning the nature of such processes, and, particularly, the function of the contact material and the manner in which such function is performed. For example, workers in the art have at one time or another suggested that the function of the contact material involves a purely physical phenomenon, an adsorption-desorption process either of atomic or molecular oxygen and either on the surface or occluded within the solid material, oxidation-reduction utilizing multivalent metals capable of oxidation-reduction, adsorption and desorption of the organic materials on the solid materials, a free radical mechanism, etc. Consequently, the solid materials utilized are referred to variously as "contact materials", "promoters", "activators" and "catalysts". Accordingly, in order to avoid functional categorization, the terms "solid contact material" or "solid contact materials" will be utilized in the present application.

Since many processes of the prior art are based on the theory that the contact materials function via adsorption-desorption of oxygen, oxidation-reduction, etc., such processes are operated in a cyclic manner by passing an oxidizing gas over the contact material, then contacting the feedstock with the oxygen containing contact material, and, thereafter, reactivating or regenerating the contact material by again passing free oxygen containing gas thereover. Such processes thus require undesirably high temperatures, are energy intensive, since the exothermic and endothermic reactions occur separately, equipment costs are high, because of the necessity for rapid cycling, and the contact material's useful life is comparatively short.

From the above, it is quite clear that the suitability of contact materials for the oxidative conversion of organic compounds is unpredictable. It is, therefore, highly desirable that new and improved contact materials for such use be developed, and that improved processes utilizing such contact materials be provided, particularly processes which lower the temperatures necessary, lower the energy requirements, are capable of being carried out in a continuous manner, extend the useful life of the contact material, improve the conversion of the feedstock and improve the selectivity to the desired products.

Of the various feedstocks for the organic chemical and petrochemical industries, olefins, such as ethylene and propylene are of particular interest and have become major feedstocks. Of these, ethylene is by far the more important chemical feedstock since the demand for ethylene feedstocks is about double that for propylene feedstocks. Consequently, there is a definite need for materials and processes for the conversion of relatively inexpensive feedstocks to ethylene. At the present time, ethylene is produced almost exclusively by the dehydrogenation or pyrolysis of ethane and propane, naptha and, in some instances, gas oils. About 75% of the ethylene is produced at the present time by steam cracking of ethane and propane derived from natural gas, since natural gas contains from about 5 volume percent to about 60 volume percent of hydrocarbons other than methane, with the majority being ethane. However, relatively severe conditions, particularly temperatures in excess of about 1000° C., are required and, as indicated, such processes are highly energy intensive. In order to reduce the severity of the conditions, particularly temperature, numerous proposals to catalyze pyrolytic reactions have been made. While some of these processes do, in fact, reduce the severity of the conditions, the conversion of the feedstock and the selectivity to ethylene are still quite low. Of particular interest in this phase of the art, is the oxidative conversion of methane to higher hydrocarbons, particularly ethylene and ethane. However, many of the processes for such oxidative conversion which have been proposed, are subject to some or all of the previously mentioned deficiencies and to date are not commercially viable.

SUMMARY OF THE INVENTION

It is therefore an object of the present invention to provide an improved composition of matter and method of utilizing the same which overcomes the above and other disadvantages of the prior art. Another object of the present is to provide an improved composition of matter. Yet another object of the present invention is to provide an improved contact material for the oxidative conversion of organic compounds to other organic compounds. Still another object of the present invention is to provide an improved contact material for the oxidative conversion of organic compounds to other organic compounds, in the presence of a free oxygen containing gas. A further object of the present invention is to provide an improved method for the oxidative conversion of organic compounds to other organic compounds. Another and further object of the present invention is to provide an improved method for the oxidative conversion of organic compounds to other organic compounds, in the presence of a free oxygen containing gas. A still further object of the present invention is to provide an improved method for the oxidative conversion of alkane hydrocarbons to other hydrocarbons. Another and further object of the present invention is to provide an improved method for the oxidative conversion of alkane hydrocarbons to other hydrocarbons, in the presence of a free oxygen containing gas. A further object of the present invention is to provide a method for the oxidative conversion of organic compounds to other organic compounds, which results in improved conversion of feedstock. Yet another object of the present invention is to provide a method for the oxidative conversion of organic compounds to other organic compounds, which results in improved selectivity to desired products. A further object of the present invention is to provide a method for the oxidative conversion of organic compounds to other organic compounds, which results in improved conversion of feedstock and an improved selectivity to desired products. Another and further object of the present invention is to provide a method for the oxidative conversion of organic compounds to other organic compounds, which utilizes temperatures below those of known processes. A still further object of the present invention is to provide a method for the oxidative conversion of organic compounds to other organic compounds, which reduces the energy requirements thereof. Another object of the present invention is to provide a method for the oxidative conversion of organic compounds to other organic compounds, which can be carried out in a continuous manner. Yet another object of the present invention is to provide a method for the oxidative conversion of organic compounds to other organic compounds, which extends the useful life of the contact material utilized. These and other objects of the present invention will be apparent from the following detailed description.

The present invention provides an improved, solid composition of matter selected from the group consisting of:

(a) a component comprising: (1) at least one material selected from the group consisting of lanthanum oxides and a component comprising: (2) at least one material selected from the group consisting of halogen ions, compounds containing halogen ions, tin and compounds containing tin; and (b) a component comprising: (1) at least one material selected from the group consisting of Group IA metals and compounds containing said metals, a component comprising: (2) at least one material selected from the group consisting of lanthanum and compounds containing lanthanum, and, optionally, a component comprising: (3) at least one material selected from the group consisting of halogen ions, compounds containing halogen ions, tin and compounds containing tin.

In another aspect, the present invention relates to a contact material, of the above composition of matter, adapted to convert feed organic compounds to product organic compounds, particularly, in the presence of a free oxygen containing gas.

A further aspect of the present invention includes: a method for the oxidative conversion of feed organic compounds to product organic compounds comprising:

contacting said feed organic compounds with a solid contact material selected from the group consisting of:

(a) a component comprising: (1) at least one material selected from the group consisting of lanthanum oxides and, optionally, a component comprising: (2) at least one material selected from the group consisting of halogen ions, compounds containing said halogen ions, tin and compounds containing tin; and (b) a component comprising: (1) at least one material selected from the group consisting of Group IA metals and compounds containing said metals, a component comprising: (2) at least one material selected from the group consisting of lanthanum and compounds containing lanthanum and, optionally, a component comprising: (3) at least one material selected from the group consisting of halogen ions, compounds containing halogen ions, tin and compounds containing tin under oxidative conversion conditions sufficient to convert said feed organic compounds to said product organic compounds.

Yet another aspect of the present invention comprises a method for the oxidative conversion of feed organic compounds to product organic compounds, comprising:

contacting said feed organic compounds and a free oxygen containing gas with a solid contact material selected from the group consisting of:

(a) a component comprising: (1) at least one material selected from the group consisting of lanthanum oxides, and, optionally, a component comprising: (2) at least one material selected from the group consisting of halogen ions, compounds containing halogen ions, tin and compounds containing tin;

(b) a component comprising: (1) at least one material selected from the group consisting of Group IA metals and compounds containing said metals, a component comprising: (2) at least one material selected from the group consisting of tin and compounds containing tin, and, optionally, a component comprising: (3) at least one material selected from the group consisting of halogen ions and compounds containing halogen ions; and (c) a component comprising: (1) at least one material selected from the group consisting of Group IA metals and compounds containing said metals, a component comprising: (2) at least one material selected from the group consisting of lanthanum and compounds containing lanthanum and, optionally, a component comprising: (3) at least one material selected from the group consisting of halogen ions, compounds containing halogen ions, tin and compounds containing tin, under oxidative conversion conditions sufficient to convert said feed organic compounds to said product organic compounds.

DESCRIPTION OF THE PREFERRED EMBODIMENTS

The improved, solid composition of matter of the present invention is a solid composition of matter selected from the group consisting of:

(a) a component comprising: (1) at least one material selected from the group consisting of lanthanum oxides and a component comprising: (2) at least one material selected from the group consisting of halogen ions, compounds containing halogen ions, tin and compounds containing tin; and (b) a component comprising: (1) at least one material selected from the group consisting of Group IA metals and compounds containing said metals, a component comprising: (2) at least one material selected from the group consisting of lanthanum and compounds containing lanthanum and, optionally, a component comprising: (3) at least one material selected from the group consisting of halogen ions, compounds containing halogen ions, tin and compounds containing tin.

The above compositions of matter are particularly useful as contact materials for the oxidative conversion of feed organic compounds to product organic compounds and, particularly, for the oxidative conversion of feed organic compounds to product organic compounds, in the presence of a free oxygen containing gas. Therefore, in accordance with another aspect of the present invention, a solid contact material, adapted to convert free organic compounds to product organic compounds, is provided.

A further aspect of the present invention includes: a method for the oxidative conversion of feed organic compounds to product organic compounds, comprising:

contacting said feed organic compounds with a solid contact material selected from the group consisting of:

(a) a component comprising: (1) at least one material selected from the group consisting of lanthanum oxides and, optionally, a component comprising: (2) at least one material selected from the group consisting of halogen ions, compounds containing said halogen ions, tin and compounds containing tin; and (b) a component comprising: (1) at least one material selected from the group consisting of Group IA metals and compounds containing said metals, a component comprising: (2) at least one material selected from the group consisting of lanthanum and compounds containing lanthanum and, optionally, a component comprising: (3) at least one material selected from the group consisting of halogen ions, compounds containing halogen ions, tin and compounds containing tin under oxidative conversion conditions sufficient to convert said feed organic compounds to said product organic compounds.

Yet another aspect of the present invention comprises a method for the oxidative conversion of feed organic compounds to product organic compounds to product organic compounds comprising:

contacting said feed organic compounds and a free oxygen containing gas with a solid contact material selected from the group consisting of:

(a) a component comprising: (1) at least one material selected from the group consisting of lanthanum oxides and, optionally, a component comprising: (2) at least one material selected from the group consisting of halogen ions, compounds containing halogen ions, tin and compounds containing tin;

(b) a component comprising: (1) at least one material selected from the group consisting of Group IA metals and compounds containing said metals, a component comprising: (2) at least one material selected from the group consisting of tin and compounds containing tin, and, optionally, a component comprising: (3) at least one material selected from the group consisting of halogen ions and compounds containing halogen ions; and (c) a component comprising: (1) at least one material selected from the group consisting of Group IA metals and compounds containing said metals, a component comprising: (2) at least one material selected from the group consisting of lanthanum and compounds containing lanthanum and, optionally, a component comprising: (3) at least one material selected from the group consisting of halogen ions, compounds containing halogen ions, tin and compounds containing tin, under oxidative conversion conditions sufficient to convert said feed organic compounds to said product organic compounds.

When the term "effective amount" is utilized with reference to the composition of matter and contact materials herein, this term is meant to include more than an insignificant amount and, thus, a small amount sufficient to affect the function of the composition of matter for the purpose for which it is to be utilized.

Thus, lanthanum oxide is utilized in amounts from an effective amount to 100 Wt. % by weight. Where tin is added to lanthanum oxide the amounts of tin may be from an effective amount to near 100 wt. % of elemental tin, based on the total weight of the lanthanum oxide and any compounds containing tin which might be used. However, in this combination, tin is generally the minor component and lanthanum oxide the major component. Hence tin will usually represent from about 0.5 to about 20 wt. %, preferably, between about 0.5 to about 7 wt. %, of elemental tin, based on the total weight of the active components of the contact material. Halogen ions, in combination with lanthanum, may also vary from an effective amount to near 100% of elemental halogen, based on the total weight of the active components of the contact material, usually about 0.1 wt. % to about 5 wt. %. When tin and halogen ions are both used with lanthanum oxide the tin and halogen ions may be present in the amounts previously set forth. A convenient form of both tin and halogen ions is, for example halide.

In a combination of a Group IA metal with lanthanum and, optionally, tin and/or halogen ions, any of the components may be present in amounts from an effective to near 100% of elemental metal or elemental halogen based on the total weight of active components of the contact material. However, in this combination, the Group IA metal will usually be the minor component representing from about 0.1 wt. % to about 50 wt. %, preferably, about 0.5 wt. % to about 15 wt. % and, still more preferably, about 1 wt. % to about 5 wt. % of elemental Group IA metal, based on the total weight of the active components of the contact material, and lanthanum will comprise the balance, as the major component. When tin is present it usually will be from about 0.5 wt. % to about 20 wt. %, preferably, between about 1 wt. % and 20 wt. % of elemental tin, based on the total weight of the active components of the contact material. Halogen ions would be utilized in amounts between about 0.1 wt. % and about 5 wt. %, based on the total weight of the active components of the contact material.

The above-mentioned components can be mixed with or deposited on an "inert support material" adapted to harden or support the active materials. The term "inert support material", when utilized in this context, is meant to include any material which does not react with or exchange ions with the active components, has no significant functional effect on the production of desired or undesired products in the process for which the solid contact material is utilized and functions only as a hardening agent or support for the active components. Where such solid support material is utilized the weight of such solid support material is not included in determining the relative weights of the active components.

The Group IA metal, tin, halogen and lanthanum can be derived from any suitable source of such materials, such as metal carbonates, hydroxides, oxides, nitrates, octoates, halides, etc. The contact materials can be prepared by any suitable method for the preparation of such materials in solid form. Particularly effective techniques are those utilized for the preparation of solid catalysts. Conventional methods of such catalyst preparation include coprecipitation from an aqueous, an organic or a combination solution-dispersion, impregnation, dry mixing, wet mixing or the like, alone or in various combinations. In general, any method can be used which provides compositions of matter containing the prescribed components in effective amounts. For example, a lithium/lamthanum material may be produced by mixing lithium carbonate and lanthanum oxide in a blender with enough water to form a thick slurry. The slurry can then be dried, usually at a temperature sufficient to volatilize the water or other carrier, such as about 220° F. to about 450° F. Alternatively, lanthanum oxide pellets can be impregnated with an aqueous solution of lithium nitrate and dried. Where tin is present, the composition can be produced by impregnating lanthanum oxide pellets with a hexane solution of tin octoate and drying. In all cases, irrespective of how the components are combined, and irrespective of the source of the metal or halogen, the dried composition is calcined in the presence of a free oxygen containing gas, usually at temperatures between about 700° F. and about 1200° F. for from 1 to about 24 hours. While the exact form of the metals in the resultant composition is not known, it is believed that the Group IA metals and lanthanum are predominantly in their oxide form and, where halogen is present, it is in the form of a halide.

As previously indicated, these compositions of matter and contact materials are particularly useful for the oxidative conversion of feed organic compounds to product organic compounds, and, particularly, the conversion of feed organic compounds to product organic compounds, in the presence of a free oxygen containing gas. Processes of this character include the oxidative dehydrogenation of hydrocarbons, particularly alkanes having 2 to 7 carbon atoms, to other hydrocarbons, particularly ethylene, the oxidative methylation of toluene, in the presence of methane, to ethyl benzene and styrene, the oxidative conversion of toluene to stilbene, the oxidative methylation of acetonitrile, in the presence of methane, to acrylonitrile and $C_2+$ hydrocarbons and the oxidative methylation of other hydrocarbons. The compositions of matter and contact materials of the present invention are particularly useful for the oxidative conversion of methane to higher hydrocarbons, particularly the oxidative conversion of methane to ethylene, in the presence of a free oxygen containing gas. Accordingly, the utility of the novel compositions of matter and contact materials and the novel processes of the present invention will be illustrated and exemplified by reference to a reaction for the conversion of methane to higher hydrocarbons, in the presence of a free oxygen containing gas. It is to be understood that the conditions of operation of other oxidative conversion processes will differ somewhat. However, such conditions are either known to those skilled in the art or can be readily optimized by one skilled in the art by simple, conventional experiments.

In addition to methane, the hydrocarbon feedstock, employed in the method of the present invention, may contain other hydrocarbon or non-hydrocarbon components. The presence of ethane, propane and the like are not detrimental. It has been found that carbon dioxide and water are not detrimental, since they are most often products of the process. It has also been found that inert gases, such as nitrogen, helium and the like are not detrimental. Consequently, the method of the present invention can effectively utilize any conventional natural gas. To the extent significant amounts of hydrogen sulfide are present in the natural gas, it is desirable to first remove the hydrogen sulfide, since it is believed that excessive amounts of this material can be detrimental to the method. Accordingly, a relatively inexpensive source of methane, namely natural gas, can be employed without expensive separation or processing of the components thereof, with the exception of the relatively inexpensive removal of excess amounts of hydrogen sulfide. Other sources of methane or methane-containing gases can also be utilized.

The free oxygen containing gas may be any suitable free oxygen containing gas, such as oxygen, oxygen-enriched air or air. The method of the present application has been effectively carried out utilizing air as a source of oxygen.

When utilized in the present invention, the term "diluent gas" is meant to include any gaseous material or material, which is in vapor form during the reaction, present in the methane- containing gas, the free oxygen containing gas or in the form of an added gas vapor.

The volumetric ratio of methane to free oxygen should be in excess of about 1/1, preferably it is between about 1/1 and about 30/1 and still more preferably between 4/1 and about 15/1. It has been found that a ratio of methane to free oxygen of at least about 1/1 is necessary, in accordance with the present invention, in order to obtain maximum conversion of methane and high selectivity to higher hydrocarbons, particularly ethylene.

In the present invention, it has been found that the method can be carried out between two extremes, namely, low conversion of methane/high selectivity to higher hydrocarbons, particularly ethylene, and high conversion of methane/low selectivity to the higher carbons, particularly ethylene. The process parameters (space velocity, temperature, and reactant partial pressure) can, to some extent, be used to control the reaction at the desired point between these two limits. Consequently, the reaction conditions may vary between broad limits.

The temperature is preferably at least about 500° C. and will generally vary between about 500° C. and about 1500° C. However, in order to obtain high conversions of methane and high selectivities to ethylene and ethane, the temperature is preferably between about 500° C. and about 900° C. and most desirably between about 600° C. and about 800° C.

It has also been found that, as the partial pressure of oxygen is increased, the selectivity to higher hydrocarbons decreases and the selectivity to carbon dioxide increases and vice versa. Total pressures may vary anywhere from around 1 atmosphere to about 1500 psi but are preferably below about 300 psi and ideally below about 100 psi.

Methane flow rates can also bary over a wide range, for example, from 0.5 to 100 cubic centimeters per minute per cubic centimeter of contact material. Preferably, however, the rate is between about 1.0 and about 20 cubic centimeters per minute per cubic centimeter of contact material.

The total flow velocities of all gaseous materials, including diluents, through a fixed bed reactor, may be at any rate effective for the oxidative conversion reaction. For example from 50 to 10,000 GHSV and preferably from 500 to 5000 GHSV.

In addition to the high conversion of methane and high selectivity to ethylene and ethane, attainable in accordance with the present invention, the contact materials are not readily poisoned and will tolerate the presence of water, carbon dioxide, carbon monoxide and the like. In addition, the contact materials appear to be long lived, with no noticeable deactivation problems. Concomitantly, the process can be carried out continuously in fixed, moving, fluidized, ebullating or entrained bed reactors/

The following examples illustrate the nature and advantages of the present invention.

The contact materials of the examples were prepared by aqueous slurrying, drying and calcining.

In the runs of the examples, the contact material was loaded in a quartz reactor having a thermocouple well centered in the contact material bed. The reactor was brought up to temperature under nitrogen or air and, thereafter, methane and air (or nitrogen or oxygen) flow was begun. The gas inlet system included electronic flow measurement, a three-zone furnace for heating reactant gases and the contact material and a downstream analysis system. The reactor effluent was snap sampled, at any desired time, and analyzed for all paraffins and olefins between $C_1$ and $C_4$ and $N_2$, $O_2$, CO and $CO_2$, by gas chromatography. All contact materials are referred to in terms of weight percent of the designated element, based on the total weight of the active components of the contact material.

The variables and results of this series of tests are set forth in the Table below. Conversion is mole percent of methane converted. Selectivity is based on mole percent of methane feed converted to a particular product. The $CH_4$ rate can be expressed as cc/min/cc of contact material. For example, when 70 cc/min of $CH_4$ was fed to a reactor containing 20 cc of catalyst, the flow rate would be 3.5 cc/min of $CH_4$/cc of contact material. The volumetric ratio of $CH_4$ to free oxygen containing gas and other gases is also given in terms of cc/min of $CH_4$ per cc/min of free oxygen containing gas or other gases (air or $N_2$) present. The promoter metals of the contact materials were in their oxide form and, as previously indicated, the percent of promoter metal is the weight percent of elemental promoter metal or metals based on the total weight of the promoter metal compound or compounds and the base metal compound.

What is claimed is:

1. A method for oxidative conversion of feed organic compounds comprising methane to product organic compounds comprising hydrocarbons, comprising:
   contacting said feed organic compounds and an oxygen containing gas with a solid contact material comprising lanthanum oxide under conditions sufficient to convert said feed organic compounds to said product organic compounds.

2. A method in accordance with claim 1 wherein the gas comprising methane is natural gas.

3. A method in accordance with claim 1 wherein the temperature of contacting is at least about 500° C.

4. A method in accordance with claim 1 wherein the temperature of contacting is between about 500° C. and about 1500° C.

5. A method in accordance with claim 1 wherein the oxidative conversion is carried out in the presence of a free oxygen-containing gas.

6. A method in accordance with claim 5 wherein the volumetric ratio of methane to free oxygen is at least about 1/1.

7. A method in accordance with claim 5 wherein the volumetric ratio of methane to free oxygen is between about 1/1 and 30/1.

8. A method for the oxidative conversion of feed organic compounds comprising methane to product organic compounds comprising higher hydrocarbons, comprising:
   contacting said feed organic compounds and an oxygen containing gas with a solid contact material comprising: (a) lanthanum oxide and (b) at least one promoter selected from the group consisting of Group IA metals.

9. A method in accordance with claim 8 wherein the Group IA metal is selected from the group consisting of lithium, sodium and potassium.

10. A method in accordance with claim 8 wherein the Group IA metal is in the predominately oxide form.

11. A method in accordance with claim 8 wherein the oxidative conversion is carried out in the presence of a free oxygen-containing gas.

12. A method in accordance with claim 11 wherein the volumetric ratio of methane to free oxygen is at least about 1/1.

TABLE

| Run No. | Contact Material | Volume $CH_4$/Air | Volume of Con. Mat. | Sample Time (min) | Temp (°C.) | Conversion | Selectivity % | | | | | | |
|---|---|---|---|---|---|---|---|---|---|---|---|---|---|
| | | | | | | | $C_2=$ | $C_2$ | $C_2$'s | $C_3=$ | $C_3$ | $CO_2$ | CO |
| 1 | $La_2O_3$ | 70/80 | 20 cc | 48 | 710 | 16.3 | 23.6 | 20.7 | 44.3 | 1.3 | 1.8 | 36.6 | 9.7 |
| | | | | 85 | 710 | 15.2 | 23.1 | 28 | 51.1 | 1.4 | 2 | 35.4 | 10.2 |
| 2 | Li(3%)/$La_2O_3$ | 70/80 | 20 cc | 5 | 702 | 17.9 | 50 | 34.5 | 84.5 | 5.5 | 3 | 5.7 | 0 |
| | | | | 40 | 704 | 18.1 | 51.7 | 34.4 | 85.1 | 5.6 | 2.9 | 3.7 | 0 |
| | | | | 90 | 704 | 17.2 | 52.6 | 34.2 | 86.8 | 5.7 | 2.5 | 5 | 0 |
| | | | | 130 | 712 | 16.7 | 51.6 | 29.6 | 81.2 | 5.4 | 2 | 8.1 | 2.1 |
| | | | | 172 | 709 | 20.5 | 38.9 | 22.4 | 61.3 | 3.9 | 1.4 | 29.4 | 3.9 |
| | | | | 275 | 709 | 20.5 | 38.9 | 22.5 | 61.4 | 0 | 0 | 34.6 | 3.9 |
| 3 | Na(3%)/$La_2O_3$ | 104/104 | 25 cc | 13 | 702 | 13.9 | 29.4 | 47.1 | 76.5 | 2.1 | 3.3 | 17.5 | 0.7 |
| | | | | 54 | 703 | 14.4 | 31.4 | 43.1 | 74.5 | 2.6 | 2.8 | 19.4 | 0.7 |
| | | | | 97 | 700 | 15.2 | 30.4 | 37.3 | 67.7 | 2.8 | 2.5 | 25.9 | 1.1 |
| | | | | 157 | 700 | 15.8 | 31.6 | 29.9 | 61.5 | 2.5 | 1.8 | 31.6 | 1.5 |
| 4 | K(3%)/$La_2O_3$ | 104/104 | 25 cc | 12 | 697 | 15.7 | 28.6 | 41.7 | 70.3 | 4 | 4.9 | 20.4 | 0.6 |
| | | | | 49 | 701 | 14.9 | 27.7 | 40.6 | 68.3 | 2.2 | 3.1 | 25.4 | 0.9 |
| | | | | 84 | 701 | 15.6 | 26.1 | 37.9 | 64 | 2.4 | 3 | 29.4 | 1 |
| 5 | Li(3%)/$SnO_2$ | 70/80 | 20 cc | 5 | 697 | 12.7 | 4.4 | 13.8 | 18.2 | — | — | 81.7 | — |
| | | | | 40 | 703 | 13.3 | 9.5 | 21.5 | 31 | — | 0.4 | 65.4 | 3.2 |
| 6 | Li(3%)/$SiO_2$ | 70/80 | 20 cc | 5 | 716 | 2.9 | — | — | — | — | — | 33.4 | 66.5 |
| | | | | 45 | 721 | 2.1 | 11.3 | — | 11.3 | — | — | 26.9 | 61.7 |
| 7 | Li(3%)/$Al_2O_3$ | 70/80 | 20 cc | 40 | 700 | 15.0 | — | 3.0 | — | — | — | 64.0 | 33.0 |

While specific materials, equipment, conditions and modes of operation have been set forth herein, it is to be understood that these specific recitals are by way of illustration and to set forth the best mode only, and are not to be considered limiting.

13. A method in accordance with claim 11 wherein the volumetric ratio of methane to free oxygen is between about 1/1 and 30/1.

14. A method in accordance with claim 8 wherein the gas comprising methane is natural gas.

15. A method in accordance with claim 8 wherein the temperature of contacting is at least about 500° C.

16. A method in accordance with claim 8 wherein the temperature of contacting is between about 500° C. and about 1500° C.

* * * * *